US010006858B2

(12) United States Patent
Hart et al.

(10) Patent No.: US 10,006,858 B2
(45) Date of Patent: *Jun. 26, 2018

(54) PORTABLE DEVICE FOR MONITORING ENVIRONMENTAL CONDITIONS

(71) Applicant: TZOA/Clad Innovations Ltd., San Francisco, CA (US)

(72) Inventors: Kevin R. Hart, Port Coquitlam (CA); Taylor Cooper, Coquitlam (CA); Vlad Lavrovsky, Vancouver (CA); Justin Lam, Vancouver (CA)

( * ) Notice: Subject to any disclaimer, the term of this patent is extended or adjusted under 35 U.S.C. 154(b) by 12 days.

This patent is subject to a terminal disclaimer.

(21) Appl. No.: 15/135,267

(22) Filed: Apr. 21, 2016

(65) Prior Publication Data

US 2017/0023458 A1    Jan. 26, 2017

Related U.S. Application Data

(60) Provisional application No. 62/151,329, filed on Apr. 22, 2015.

(51) Int. Cl.
*G01N 15/06* (2006.01)
*G01N 15/02* (2006.01)
(Continued)

(52) U.S. Cl.
CPC .......... *G01N 21/53* (2013.01); *G01N 15/0211* (2013.01); *G01N 2001/2276* (2013.01);
(Continued)

(58) Field of Classification Search
CPC ............... G01N 21/53; G01N 15/021; G01N 2015/0693; G01N 2001/2276; G01N 2201/0221; G01N 2201/0612
See application file for complete search history.

(56) References Cited

U.S. PATENT DOCUMENTS 3,535,531 A    10/1970    Neitzel
3,819,269 A     6/1974    Duvall et al.
(Continued)

FOREIGN PATENT DOCUMENTS

CN    203310444 U    11/2013
WO    2009144508      12/2009

OTHER PUBLICATIONS

"Size Spectrometry of Aerosols Using Light Scattering from the Cavity of a Gas Laser" R. Schehl, S. Ergun, and A. Headrick: Review of Scientific Instruments 44, 1193 (1973).*
(Continued)

*Primary Examiner* — Dominic J Bologna
(74) *Attorney, Agent, or Firm* — Gina M. Lupino (57) ABSTRACT

A portable environment quality monitor having an enclosure to enclose and protect the monitor from an environment and for attaching to a user's clothing or jewelry. The enclosure includes a controlled airflow intake for receiving air from the environment in which the monitor is worn for forming an airflow sampling path and for laminarizing the airflow in the sampling path. A sensor, having a sensing region that directs the laminar airflow into the sensing region. A processor is connected to a light scattering aerosol spectrometer (LSAS) that is configured to receive, process and translate photodiode current peaks into particle counts and sizes detected in the air. The processor is also coupled to a memory for storing data corresponding to the particle counts and sizes detected in the environment. The processor further includes an interface to communicate with a host for allowing a user to monitor and track environment conditions.

14 Claims, 4 Drawing Sheets

(51) Int. Cl.
  *G01N 21/53* (2006.01)
  *G01N 1/22* (2006.01)
(52) U.S. Cl.
  CPC ............... *G01N 2015/0693* (2013.01); *G01N 2201/0221* (2013.01); *G01N 2201/0612* (2013.01)

(56) References Cited

U.S. PATENT DOCUMENTS

| | | | |
|---|---|---|---|
| 3,833,305 A * | 9/1974 | Porter | G01N 21/15 |
| | | | 250/573 |
| 4,783,599 A | 11/1988 | Borden | |
| 5,085,500 A | 2/1992 | Blesener | |
| 5,132,548 A | 7/1992 | Borden et al. | |
| 5,262,741 A | 11/1993 | Kitakubo | |
| 5,534,999 A | 7/1996 | Koshizuka | |
| 5,684,585 A | 11/1997 | Girvin et al. | |
| 5,870,190 A | 2/1999 | Unger | |
| 7,088,447 B1 | 8/2006 | Bates et al. | |
| 8,009,290 B2 | 8/2011 | Unger | |
| 8,494,773 B2 | 7/2013 | Jensen et al. | |
| 8,603,772 B2 | 12/2013 | Debreczeny et al. | |
| 2004/0083064 A1* | 4/2004 | Wyatt | G01N 1/2202 |
| | | | 702/28 |
| 2008/0106736 A1 | 5/2008 | Graves et al. | |
| 2011/0265706 A1* | 11/2011 | Nicholls | A41D 19/0027 |
| | | | 116/201 |
| 2013/0317379 A1* | 11/2013 | Brimer | A61B 5/087 |
| | | | 600/538 |
| 2014/0163927 A1 | 6/2014 | Molettiere et al. | |
| 2014/0243617 A1* | 8/2014 | LeBoeuf | A61B 5/0059 |
| | | | 600/301 |
| 2015/0153275 A1* | 6/2015 | Park | G01N 33/0036 |
| | | | 356/336 |
| 2016/0025628 A1* | 1/2016 | Kim | G01K 13/02 |
| | | | 356/72 |

OTHER PUBLICATIONS

Sirinivas Devarakonda, Parveen Sevusu, Hongzhang Liu, Ruilin Liu, Liviu Iftode, Badri Nath, Real-time Air Quality Monitoring Through Mobile Sensing in Metropolitan Areas (research paper), Department of Computer Science, Rutgers University, Piscataway, NJ USA. 2013.

Matthias Budde, Rayan El Masri, Till Riedel, Michael Beigl; Enabling Low-Cost Particulate Matter Measurement for Participatory Sensing Scenarios; TECO, Karlsruhe Institute of Technology (KIT), Karlsruhe, Germany; 2013.

Anna Morpurgo, Federico Pedersini, and Alessandro Reina; A low-cost instrument for environmental particulate analysis based on optical scattering; Department of Information Science, Universita degli studi di Milano via Comelico 39/41, I-20135 Milano, Italy; 2012.

* cited by examiner

PORTABLE DEVICE FOR MONITORING ENVIRONMENTAL CONDITIONS

PRIORITY CLAIM

This non-provisional application claims priority to Provisional Patent Application Ser. No. 62/151,329, entitled "Device for Environmental Monitoring and Tracking", filed on Apr. 22, 2015.

TECHNICAL FIELD

The present invention relates generally to a device for environmental monitoring and tracking. In particular, the present invention may be used to measure particulate matter floating in ambient air.

BACKGROUND OF THE INVENTION

There is a growing market demand for inexpensive environmental monitors for both research and personal health. Poor environmental conditions such as toxic air pollutants and the chemicals that form acid rain and ground-level ozone can damage trees, crops, wildlife, and bodies of water. Airborne particulate matter is among the deadliest forms of air pollution. Increased concentration of particulate matter below PM10 greatly increases risk of lung cancer with no safe minimum level. Asthma, cardiovascular disease, respiratory diseases and birth defects have also been associated with increases in airborne particulate matter concentration.

These conditions are also a detriment to the economy, resulting in thousands of workers on sick leave per day and billions of dollars lost due to reduced yields of agricultural crops and strain on health care systems around the world. Environmental researchers often do not have the budget to purchase multiple devices to develop data maps in order to monitor these adverse environmental conditions.

There is also a growing interest for consumers to gauge their overall health and collect personal environmental exposure statistics. Poor environmental conditions are a concern for those with health problems such as people with sensitive respiratory systems or the elderly with heart diseases. Environmental trackers may be used for monitoring these conditions at home, in the office, during a commute or exercise routine.

Environmental data would typically include air quality, temperature, humidity, pressure, visible light and ultra-violet (UV) radiation. Light scattering aerosol spectrometers (LSAS) are typically used to measure airborne particles, which can aggravate health problems and cause throat irritation and breathing difficulties. Thermistors, thermocouples or resistance temperature detectors are typically used to monitor temperatures and communicate with the software to warn the user if there is an increased risk of heat stroke due to high ambient temperatures. Developments in microelectromechanical systems (MEMS) have made measuring humidity and pressure simple tasks that can be done with cost-effective off-the-shelf integrated circuits, MEMS Hygrometers are used to measure humidity; low humidity levels may lead to skin irritation and excessive dehydration, MEMS Barometers are used to measurement atmospheric pressure which can be indicative of changing weather conditions. Photodiodes can be used to measure UV and visible wavelength radiation. Extended and unprotected exposure to UV radiation is known to increase the risk for skin cancer. A LSAS can use humidity and temperature measurements to increase its accuracy.

Conventional techniques for measuring environmental conditions are limited by single-function monitors. Multiple devices would be required in order to measure air quality, temperature, humidity, pressure, and UV radiation. The collected data would be on separate platforms; many of which are devices and not intended to be carried around for extended periods.

Increased affordability for these sensors combined with improvements in battery, wireless and mobile computing have created conditions for the development of a low cost wearable environmental sensor. A wearable device typically is worn daily as an accessory like a watch or jewelry. Existing wearable devices are often bulky, uncomfortable, and are only able to measure a one or two environmental parameters. They typically have relatively large plastic enclosures and are not suitable for carrying around for extended periods, let alone allowing the user to wear the device and have freedom of movement during typical daily activities. Additionally, existing wearable devices are typically limited to a single user and do not support analyzing data from multiple users to create regional data maps.

There are multiple possible use cases for this technology. In one use case, the user may operate the device primarily as a personal self-monitoring health device. The user may wear the device and check the measurements throughout the day. The device will infrequently store the measured data to on-board memory and frequently sync the measured data with the application. In the second use case, the user may operate the device primarily in the research industry. The user may install the device in a certain location, leave it for a number of hours, days, or weeks, retrieve the device after this period, then sync the data with the application. The device will frequently store the measured data to on-board memory and infrequently sync the measured data with the application. This patent will focus primarily on the first use case. The alternate embodiment of the invention is the device that fulfills the second use case.

Current methods of environmental monitoring may be expensive, laborious or inconvenient. Accordingly, this results in a need for a low cost, effective method for monitoring and tracking environmental conditions.

SUMMARY OF THE INVENTION

One embodiment of the invention (also known as the device herein) provides an improved method in monitoring and tracking environmental conditions by means of a small, low-profile device. This embodiment of the device includes a plurality of environmental sensors in an enclosure to be attached or worn by the user. In this embodiment of the invention each environmental sensor is configured to measure environmental conditions within the vicinity of the person utilizing the device.

This embodiment of the invention consists of an enclosure, one or more circuit boards, a battery, a plurality of sensors and their subcomponents, one or more microcontrollers, one or more wireless communication modules, and a smartphone application and/or other interface software for a personal computer (PC). The device may also include a plurality of user interface peripherals, such as: LEDs, buttons, connectors for hardline interface, wireless charging interfaces, or application programming interface (API). The enclosure may consist of plurality of the following components: a top cover, a bottom cover, a shield, a light diffuser(s), and other optical and air management components. The circuit boards contains circuits for interfacing with all electronic components and sensors, and may be of flexible or rigid construction.

This embodiment contains sensors for sensing air quality, temperature, humidity, pressure, visible light, gases and UV radiation. In this embodiment the air quality sensor is a custom built LSAS, the major components of which may include a plurality of the following components: a fan, a laser, a photodiode, driving circuitry, signal processing circuitry, a microcontroller unit (MCU), and/or digital signal processor (DSP). The LSAS is designed with baffling for stray light and air flow control, this baffling is integrated with major components of the device.

This embodiment of the invention requires wireless communications between a smartphone or PC application for user control, data processing, data visualization, communication with a cloud-based network, and any other backend peripherals. In this embodiment a microcontroller unit configured to receive and process signals produced by the environmental sensors. In this embodiment the environmental data is collected and wirelessly transmitted to a smartphone application, where the data is stored, processed and localized with data from the smartphone or the device. In this embodiment, the data is also stored in a cloud-based network.

In other embodiments the data may be transmitted with a hardline or displayed on the device or not transmitted. Other embodiments of the invention may involve wired communication with a smartphone or PC to similar effect. Further, other embodiments may involve part or all of this embodiment packaged inside OEM hardware; such an embodiment may provide an electronic (SPI, I2C, Serial or other) or wireless (Bluetooth Low Energy (BLE), WiFi, Xigbee, or other) interface to the OEM hardware.

A further embodiment of the invention provides a method for monitoring and tracking environment conditions substantially in the vicinity of a user. (See FIG. 6). This method includes the steps of enclosing a portable air quality monitor from the ambient environment 605; receiving ambient air in the monitor, the monitor having a controlled airflow intake for receiving the ambient air 610; forming an airflow sampling path and laminarizing the airflow in the sampling path 615; receiving the laminar airflow from the airflow intake and directing the laminar airflow into a sensing region 620; monitoring air quality, temperature, humidity, pressure, visible light, UV radiation, carbon dioxide, carbon monoxide, sound, nitrogen dioxide, magnetic fields, linear accelerations, angular accelerations, ozone and/or gamma, beta, an/or alpha radiation 625; receiving, processing and translating data received from Light Scattering Aerosol Spectrometer (LSAS) into particle counts and sizes detected in the air 630; and storing the data in a non-transitory computer readable medium corresponding to the particle counts and sizes detected in the environment 635 (See FIG. 6).

Consequently, for a better understanding of the present invention, its functional advantages and the specific objects attained by its uses, reference should be made to the accompanying drawings, claims and descriptive matter in which there are illustrated preferred embodiments of the invention.

DETAILED DESCRIPTION

The following detailed description is of the best currently contemplated modes of carrying out various embodiments of the invention. The description is not to be taken in a limiting sense, but is made for at least the purpose of illustrating the general principles of the invention, since the scope of the invention is best defined by the appended claims.

Enclosure

Figure 1:
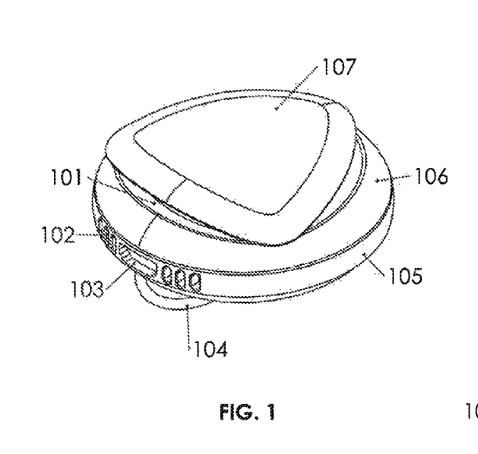
FIG. 1 is a perspective drawing of an environmental monitor tracking device, constructed according to the principles of the present invention.

One embodiment of the enclosure 605 is illustrated in FIG. 1. In this embodiment, the device is fully or partially enclosed between three or more components which are ultrasonically welded, screwed, clipped or otherwise held together. These components are referred to as collectively as the enclosure. The sensor in FIG. 3 may be partially or fully contained by this enclosure (See also FIG. 6).

The three major components of the enclosure are the bottom cover 105, top cover 106 and a shield 107. Other embodiments may consider just the top 106 and bottom 105 cover. The top 106 or bottom 105 cover may have one or more mounting/access feature for additional sensors. Alternative embodiments may have significantly different dimensions and geometry than shown in FIG. 1. Additional components may be used inside the enclosure other than the major components to aid in the function of the device. Other embodiments may have more than 5 major components. In further embodiments of the invention, the top 106 or bottom 105 cover may have one or more mounting/access features for a plurality of sensors, buttons, LEDS, and/or cables. These components may be constructed using plastic, but other materials are also suitable.

In this embodiment, there are clearance and mounting features in the top cover 106 for one or more LEDs 111 and one or more UV sensors Other embodiments may have the LEDs 111 mounted and visible from other major components. Other embodiments may have UV sensors mounted and visible from other major components.

In this embodiment of the invention, there is clearance and mounting features 103 in the bottom cover for an electrical connector. Other embodiments of the invention may have connectors mounted in other major components.

In this embodiment the top cover 106 and shield 107 make up the air intake vent for the LSAS. Other embodiments may have the air intake features in other major components.

In this embodiment the bottom cover 105 has features for the air exhaust vent for the LSAS. Other embodiments of the invention may have the air exhaust features in other major components.

In this embodiment the top cover, bottom cover 105 or shield 107 may contain features for user interface buttons.

In this embodiment any components may be used to improve environmental performance. This embodiment may also have sealed regions to resist water incursion into sensitive regions of the device. Sealing may be achieved by a plurality of gaskets, conformal coating and/or addition of sealing components or other methods. This embodiment may have intake baffle(s) 109 and exhaust baffle(s) 102 to prevent wind from interfering with the reads of the LSAS.

Additional components may be used inside the enclosure other than the major components to aid in the function of the device. These additional components may be used as a light diffuser 110 for the LEDs 111 intended for user interaction. These components may enable the mounting of connectors, sensors or circuit boards. A cavity 112 in the enclosure may also be used to as a placeholder for the circuit board. These components may prevent incursion from water or dirt. These components may restrict or enable user access to some parts of the device, to either prevent tampering, enable maintenance or allow for user customization of the device.

Figure 2:
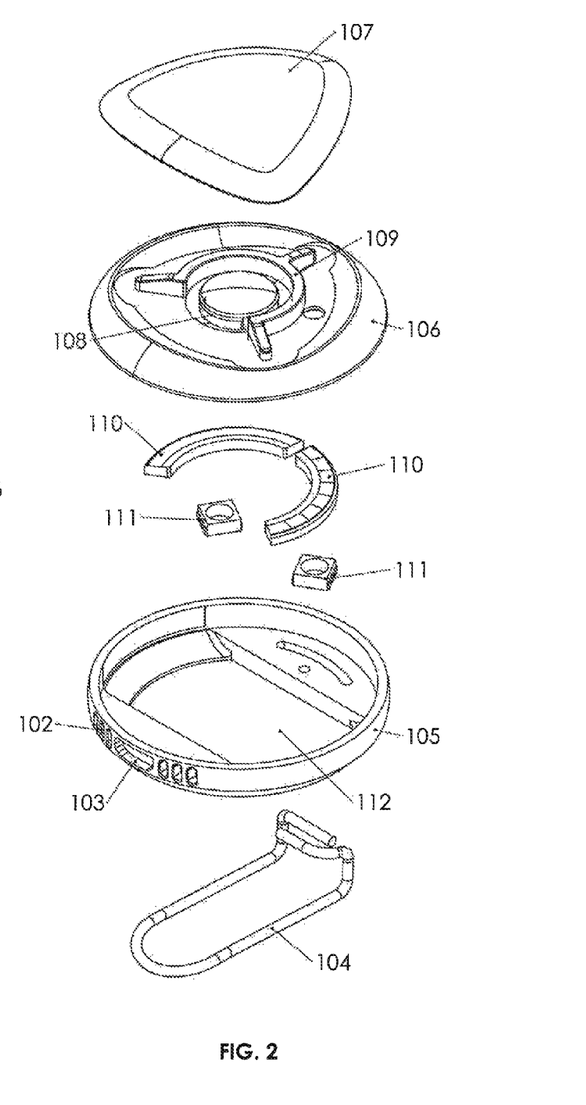
FIG. 2 is an exploded view of the device in FIG. 1.

Any component in the enclosure may have selective metal deposition/plating for aesthetic or optical reasons. The metal finish may be used to create mirrors 200 for the optical system. The enclosure may be curved to create mirrors with different optical behaviors.

Figure 3:
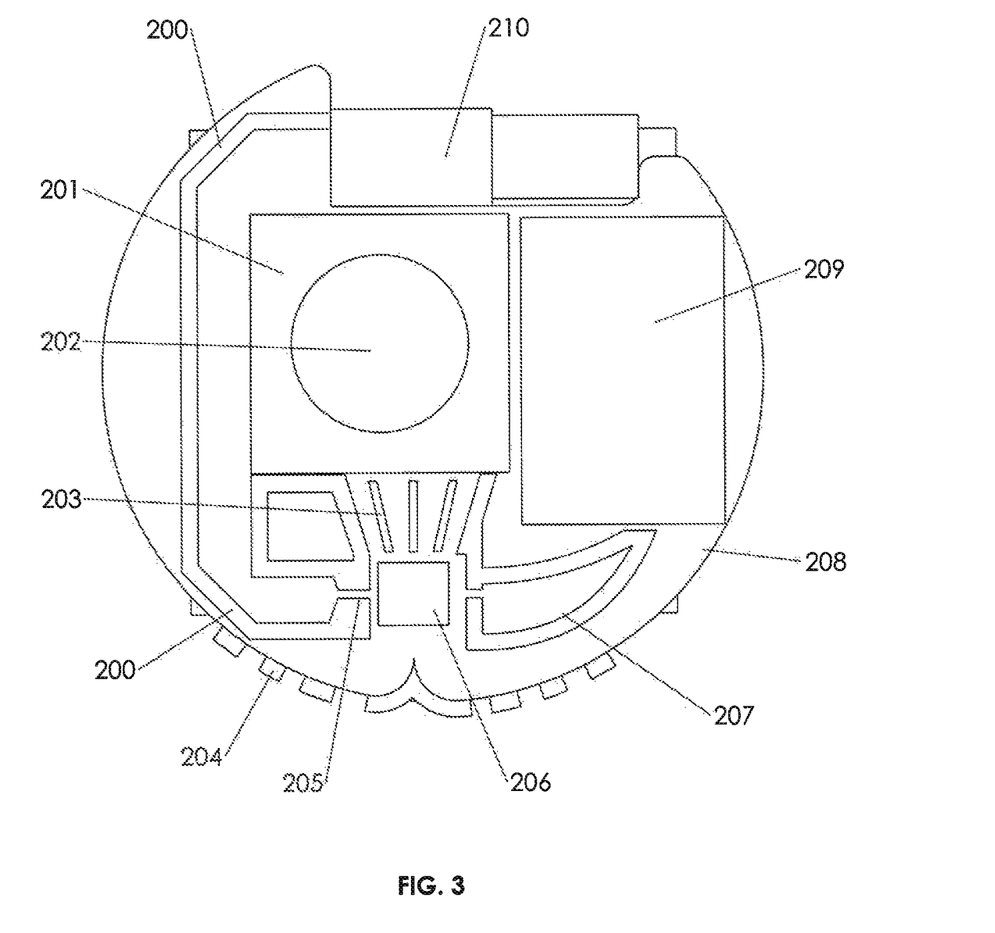
FIG. 3 is a diagrammatic top view of one embodiment of the arrangement of sensor components on the printed circuit board.

Any component in the enclosure may have an engineered surface finish for aesthetic, optical or sensor performance reasons. Any component in the enclosure may contain features for directing the airflow for the LSAS and/or other sensors, such as baffles placed before 203 and after 204 the photodiode 206. Gaskets, flexible plastic, epoxy, tape or other materials may be used to improve the function of these features. Features may be added to any part of the enclosure to reduce or increase, intake or outlet airflow velocities. Any component in the enclosure may contain overlapping baffles to prevent stray light from reaching the LSAS. Any component in the enclosure may be coated or covered with a light-absorbing paint, finish, tape or other material to improve the function of the LSAS.

In this embodiment the attachment feature 104 enables the attachment of the device to a wearable item or directly to the user. In this embodiment of the design the attachment feature is a plastic clip. In other embodiments the attachment feature 104 may be an integrated magnetic, spring loaded, or other type of clasp for attachment of the sensor to thin fabrics, bags, and/or surfaces. In other embodiments the attachment may also be a bracelet, wristband, bicep, or other type of flexible band.

In this embodiment the attachment feature 104, top cover 106, and/or bottom cover 105 may contain features for integrating with a docking station.

Docking Station

Figure 4:
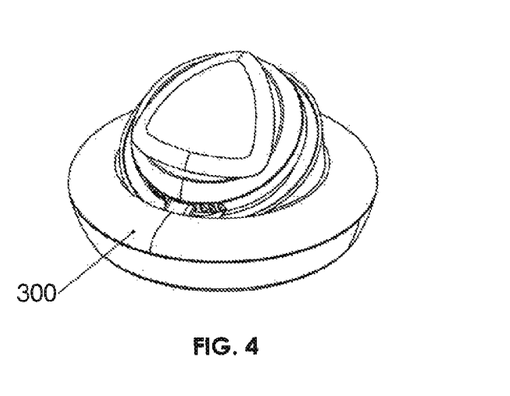
FIG. 4 is a perspective drawing of the device secured in the docking station.
Figure 5:
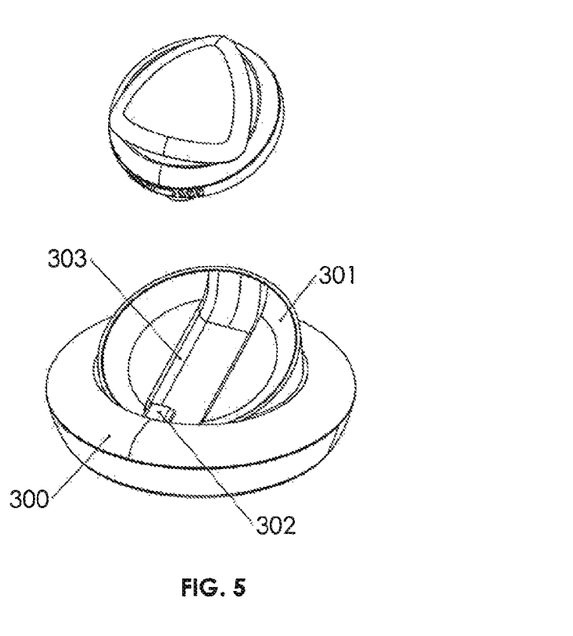
FIG. 5 is an exploded view of the docking station in FIG. 4.

One embodiment of the docking station is illustrated in FIG. 4. The docking station 300 is intended to be stationary and to improve usability of the device. The docking station may contain a connector 302 for charging or communicating with the device. The docking station may contain alignment features to align the device with the connector and to hold the device in a specific orientation while the device is in the docking station. These alignment features may include a cavity of the bottom enclosure 301 and/or a cavity of the attachment feature 303. The docking station may contain latching features to hold the device in place once it is seated. These latching features may be magnetic or spring based.

One embodiment of the dock may comprise a small compartment within the enclosure to allow the user to place additional shields inside. Another embodiment of the dock may comprise features on the exterior of the enclosure to hang the shields. The method of securing the shields to the enclosure may use the same feature on the device to secure the shield.

In other embodiments the docking station may be designed for mobility or to enhance wear-ability or battery life of the device. In the other embodiments the device may contain electronics or batteries.

Light Scattering Aerosol Spectrometer

Figure 6:
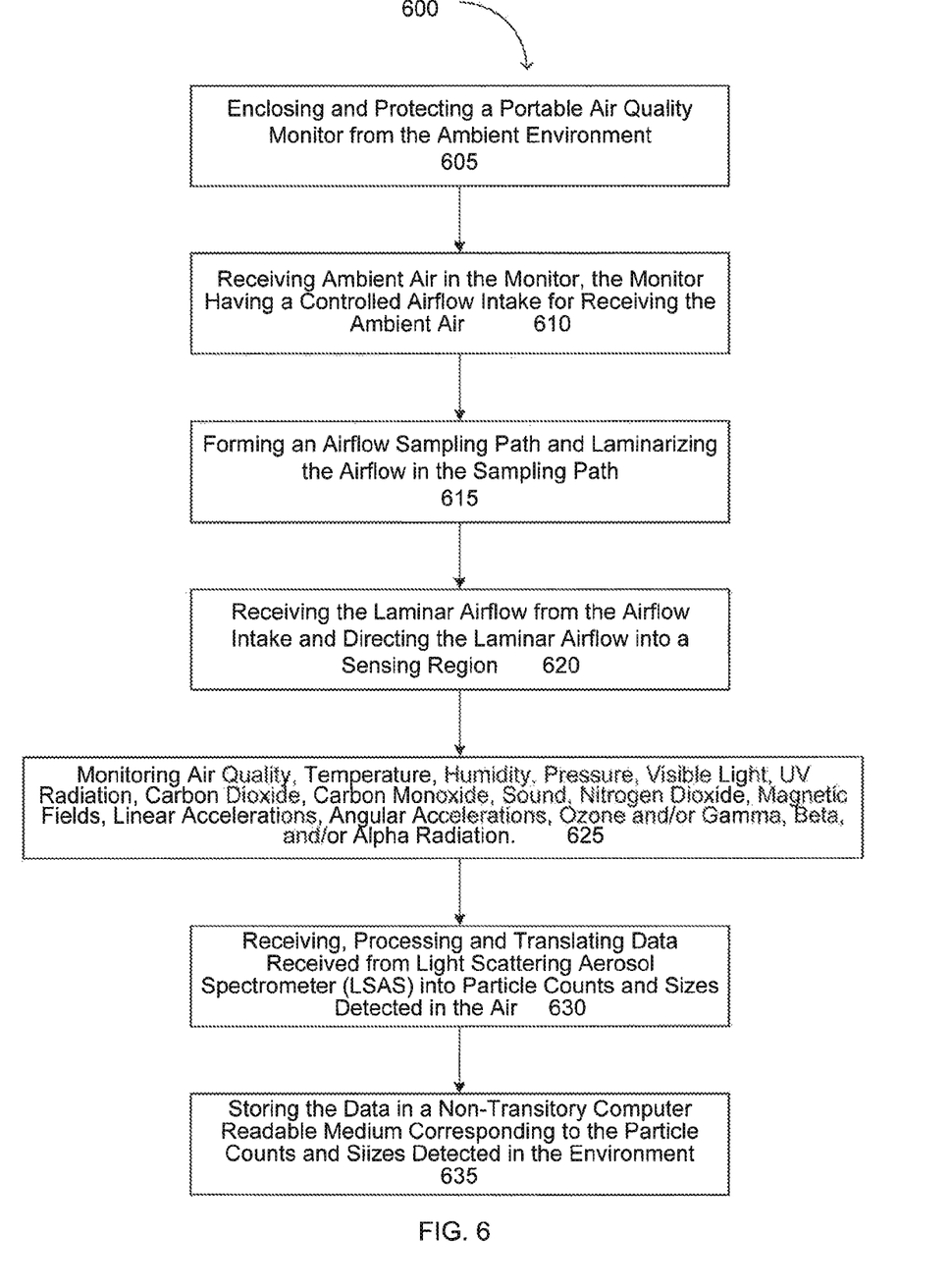
FIG. 6 refers to an execution diagram for the method of monitoring and tracking environment conditions substantially in the vicinity of a user.

A major component of the device is the integrated light scattering aerosol spectrometer (LSAS) for air quality monitoring. The LSAS is capable of counting and sizing air particulate 630 from ~0.5 μm to 20 μm. The exact specifics of operation for the LSAS are beyond the scope of this patent, but will be described in brief here. The LSAS is integral to the design of the device because of its relative complexity and size.

In this embodiment of the invention, the LSAS is comprised of the following major components: a laser assembly 210 consisting of a laser diode, enclosure, heat sink, and lens; one or more mirrors or mirrored surfaces 200; one or more sets of baffles/apertures 205 for removing unfocused laser light, a photodiode 206, a beam dump 207 and a fan 201. These components may be mounted on a circuit board 208, which may be seated in the enclosure cavity 112.

In this embodiment an integrated transimpedance amplifier, analog to digital converter (ADC), microcontroller unit (MCU), digital signal processor (DSP) are used to translate photodiode current peaks into particle counts and sizes.

Other embodiments may also consist of a plurality of these components. The mirrors 200 may be oriented to reduce the device foot print well maintaining require beam geometry for sensing. The laser beam 212 is focused and directed across the photodiode 206 perpendicular to the direction of airflow created by the fan 201, particles passing through the beam create a current in the photodiode 206 (See also FIG. 6). The LSAS has a transimpedance amplifier circuit to amply the current to a voltage that can be read by an ADC. The digital signal is then filtered and processed by an MCU, DSP and/or other signal processing electronics. Stray light is prevented from reaching the photodiode 206 with overlapping baffles 203. Air flow is shaped and directed in a laminar 615 fashion over the photodiode 206 (See also FIG. 6).

To aid in the function of the LSAS this embodiment may be modified or enhanced through the following methods. Additional components may be used inside the enclosure other than the major components to aid in the function of the device. Any part of the enclosure may have selective metal deposition/plating for aesthetic or optical reasons. The metal finish may be used to create mirrors for the optical system. The enclosure may be curved to create mirrors with different optical behaviors. Any part of the enclosure may have an engineered surface finish for aesthetic or optical reasons. Any part of the enclosure may be coated or covered with a light-absorbing paint, finish, tape or other material.

Any part of the enclosure 605 may contain features for directing the airflow 620 for the sensor. Gaskets, flexible plastic, epoxy, tape or other materials may be used to improve the function of these features. Features may be added to any part of the enclosure to reduce or increase intake or outlet airflow velocities 610. In one embodiment, the airflow induced by the fan intake 202 may enter the device through the gap 101 below the shield 107 and through the enclosure opening 108 to the sensor cavity 112 (See FIG. 9). Any part of the enclosure may contain overlapping baffles to prevent stray light from reaching the sensor. In this and other embodiments of the invention, the enclosure may have features to enable access to the LSAS for cleaning and maintenance.

In this and other embodiments of the invention, the laser and fan may have driving circuits that are controlled by the device. The control may be open or closed loop. The laser and fan may be controlled by the device to reduce or increase power draw depending on battery conditions, charging state and user input. The MCU, DSP, or signal processing electronics may have their power usage controlled by the device depending on battery conditions, charging state and user input.

Device Electronics

In this embodiment one or more circuit boards and/or one or more cable assemblies are used to mount the various electrical components of the sensor. In this embodiment of the invention, all circuitry in the device may be able to be placed in a low-power or sleep mode to preserve device battery life. Reactivation from sleep mode may be timed by a single microcontroller or may require interaction from the user, either by accessing a button on the device or sending a command by BLE. The low power mode may do a plurality of the following to save power: reduce processor clock frequency, decrease processor operations per clock cycle, cut power to any peripheral systems, use an integrated low-power/sleep mode for any component/sensor or reduce measurement frequency or any other method not discussed here.

In use, power saving, sleep mode and power resets of peripheral components may be enabled by MCU controlled switches, relays, BJTs, FETs, or other control method. In this embodiment there may be zero or more user interfaces. These interfaces may be made up from a plurality of the follow interface devices: tactile switches, infrared switches/sensors, capacitive touch sensors, ultrasonic sensors, resistive sensors and/or other interface devices. These sensors may be mounted directly on a PCB or mounted the enclosure and connected to the PCB with a cable assembly. The enclosure may have cutouts or depression features to enable actuation of these interfaces and to improve the user interaction with these devices. In other embodiments there may be a liquid crystal display (LCD) with text for displaying sensor readings, battery state of charge, time, sampling/sensing rate or frequency, calibration parameters, device ID, firmware ID or any other information relating to the device.

In this embodiment of the invention, LEDs may be mounted or connected via cable assemblies to one or more circuit boards. In this embodiment, these LEDs may be used to convey the following information to the user: sensor readings, battery state of charge, battery charging or discharging, device on, device tethering, device in tethering mode, device tethered, button feedback, self-cleaning mode, maintenance required, or other information related to the device. In this embodiment, the LEDs may be tricolor or monochrome. The LEDs may be enabled to act as a flashlight. In this embodiment drivers for the LEDs are integrated in the one or more circuit boards. In other embodiments the LEDs may have integrated drivers.

In this embodiment the device is powered with a battery. Other embodiments may use external power supplies. Other embodiments may allow the smart phone or other devices to power the device directly over a cable. The battery in this embodiment may be a single or a two cell lithium ion battery. This embodiment may contain a constant current/constant voltage charge circuit. This circuit may have a under voltage lock out circuit to protect the battery. This circuit may use a switching or linear regulator to adjust input voltage to battery voltage levels. This circuit may use a switching or linear regulator to adjust output voltage for sensor operation. This embodiment may contain circuitry for state of charge measurement, including but not limited to: circuitry for charge integration, circuitry for voltage translation and algorithms for interpreting this and other factors.

In this embodiment the device is charged by a cable or by a docking station with an integrated electrical connection. The cable connection to the device may be made with a male micro USB 2.0 B, male micro USB 2.0 AB, male micro USB 3.0 B or some embodiment of a custom connector. The cable connection to the device may also be made with an off the shelf or custom PCB edge connector, an off the shelf or custom pogo/spring pin connector or other custom connector. This connection may be latched for stability and connector safety. The latching may be achieved magnetically or with clipping features. The cable connection may be made directly to a PCB mounted female jack, gold plated pads or fingers, or to a connector mounted into the enclosure and connected to the PCB with a wire.

In this embodiment of the invention, the connection will provide 5V power and serial communication with the device. The serial communication may or may not be used to update the device's firmware or calibration. Other embodiments may use wireless charging based on existing standards such as Qi or Rezence, or a custom wireless charging interface. The wireless charging interface may be integrated into the docking station for this embodiment. The docking station may be powered with 5V DC through a USB port and/or 120V AC through a wall socket adapter. Other embodiments of the connection may provide different voltages or communication interfaces. This embodiment s expected to rely on localization and time information from the BLE connected device or smart phone but other embodiments may have this hardware integrated. Other embodiments may contain an integrated GPS module. Other embodiments may contain an integrated accelerometer and/or gyroscope. Other embodiments may contain a magnetometer. Other embodiments may contain an electronic time keeping device.

EMI and on board interference shielding may be provided for individual sections of the PCB or electronic components as needed. EMI shielding may take the form of grounded metal baffles, grounded metal covers, staggered operation of components/sensors, or other methods not mentioned here. On board interference shielding may take the form of guard traces, power and ground planes, filtering capacitors, filtering inductors, control of power and ground trace widths, or other methods not mentioned here.

Sensor Electronics

This embodiment of the device contains sensors for sensing air quality, temperature, humidity, pressure, visible light, gases and UV radiation 625. Other embodiments may contain a plurality of sensors including but not limited to sensors for detecting: air quality, temperature, humidity, pressure, visible light, UV radiation, carbon dioxide, carbon monoxide, sound, nitrogen dioxide, nitrous oxides, magnetic fields, linear accelerations, angular accelerations, ozone, and/or gamma, beta, and/or alpha radiation 625 (See FIG. 6).

Aspects related to the electrical interface of the LSAS are covered here; other design details for the LSAS responsible for sensing air quality are covered in the previous sections and will not be discussed here. Communication between the LSAS and device MCU may be accomplished by a plurality of the following protocols: analog signaling, I2C, SPI, DMA or any other custom or standardized serial or parallel communication protocol. In this embodiment the LSAS may provide particle counts with corresponding size bins, or one or more conditioned photodiode signals for ready interpretation on the device microcontroller, or a combination of both interfaces. In this embodiment the LSAS may or may not communicate particle size information. In this embodiment communication between the LSAS and the device MCU may allow adjustment to LSAS calibration parameters, sensing frequency, sensing power, sleep state or any other firmware configurable features, as well as data transfer indicated above. Any and all components for the LSAS may be integrated on the device PCB(s). These components may include but are not limited to a plurality of the following: power rail filtering, laser diode driver, fan driver, photodiode amplifier, photo diode conditioning circuitry, flow rate sensors, control electronics, signal analysis electronics, MCUs and/or DSPs. In this embodiment of the invention, the LSAS uses the same battery or power supply as the device; in other embodiments the LSAS may use a separate battery or power supply.

In this embodiment the temperature sensor and humidity sensor may be integrated in the same IC package. In this embodiment an IC measures temperature and humidity, and communicates measured values with the device MCU via an I2C communication bus. The device may sense temperature with a plurality of the following sensing methods/sensors: a resistance temperature detector, thermistor, thermocouple, infrared sensor or other sensor type. The device may sense humidity with a plurality of the following sensing methods/sensors: capacitive, resistive, thermal conductivity, gravimetric humidity sensors, and/or other sensors types not discussed here.

In this embodiment of the invention, the pressure may be sensed by one IC package. In this embodiment an IC measures pressure and communicates measured values with the device MCU via an I2C communication bus. The device may sense pressure with a plurality of the following sensing methods/sensors: a piezoresistive strain gauge, capacitive, electromagnetic, piezoelectric, optical, potentiometric and/or other sensor types not discussed here. These pressure measurements may be used to infer air flow in specific regions to help calibrate the LSAS.

In this embodiment of the invention, the UV and visible radiation may be sensed by one IC package. In this embodiment an IC measures UV index and ambient light intensity and communicates measured values with the device MCU via an I2C communication bus.

In this embodiment the sensor used for detecting scattered light is a photodiode with integrated circuitry; other embodiments may use other sensors 630 (See FIG. 6).

In this embodiment any measurement IC may be placed on a PCB or cable assembly to improve measurement accuracy.

Other embodiments of the invention may use a plurality of sensors to make measurements in a variety of locations on the device. Other embodiments may communicate with sensor ICs using other communication protocols including but not limited to a plurality of: I2C, SPI, DMA or any other custom or standardized serial or parallel communication protocol. Other embodiments may communicate with sensors directly by measuring analog signals from the sensor into the device MCU with an ADC. Other embodiments may use multiple instances of any of these sensors located throughout the device. Other embodiments may use analog power filtering techniques to remove noise from power lines. Other embodiments may use PCB layout techniques such as via stitching to decrease noise coupling between sensitive devices.

MCU, DSP, and Firmware

In this embodiment the device has one primary MCU that may or may not be integrated with a BLE communication module 209. This MCU is referred to as the device MCU. Other embodiments may use a plurality of device MCUs for various tasks. Other embodiments may use a plurality of DSPs for specialized tasks. In this embodiment the BLE module 209 or device MCU are responsible for connecting to and communicating with an application running on a smart phone or host device. The BLE module 209, device MCU, smart phone and/or host device may execute a BLE protocol stack in firmware to facilitate communication. The BLE protocol stack may be custom or based on a commercial protocol.

The MCU may be responsible for monitoring the sensor array and logging values into memory. These values may later be broadcast over BLE by the MCU over BLE or accessed by the BLE module 209 to be broadcast over BLE to the application, or sent via other communication method. A Kalman filter may be used to reduce background noise and interpret data from the device. This filter may be a plurality of sensor inputs as variables. A digital low pass or band pass filter may be used to filter out noise. Sensed values may be stored as integers and converted to floating point numbers by the application. The application or device may also be responsible for time stamping logged data.

The device MCU is used to receive data from and control the behavior and calibration of the LSAS. The MCU may also run algorithms for peak detection and signal processing required for LSAS operation. In this embodiment the device MCU may execute algorithms to convert particle counts into equivalent mass concentration values. In this embodiment the device MCU may execute algorithms to convert particle counts into a corresponding air quality index measurement.

In use, the LSAS sensor may indicate when device cleaning is required or measurement quality has declined. Self-monitoring for sedimentation/dust accumulation may be a function of particle counts and fan performance. The LSAS may be capable of completing a self-cleaning procedure that can be initiated by the device. The user may require manual cleaning of the device depending on the severity of sedimentation and dust accumulation. In one method of cleaning, partial disassembly of the device may be necessary. The user may be required to remove the shield and/or features of the enclosure to access the regions that require cleaning. In another method of cleaning, the user may inject a stream of compressed air through the device flow channels to remove sedimentation and dust accumulation.

The MCU (or a peripheral MCU) is also responsible for battery management. The device MCU may regulate power to all peripheral devices in this embodiment. The device MCU may pulse width modulate or otherwise throttle power to any of the peripherals to extend battery life. The MCU may be used directly for state of charge measurement of the battery; alternatively this task may be off loaded to a peripheral microcontroller.

The MCU or a peripheral MCU may be responsible for interpreting the function of the various I/O and user interface components. The MCU or peripheral MCU may change the intensity or color of a plurality of LEDs. These changes may indicate any of the following: sensor readings, battery state of charge, battery charging or discharging, device on, device tethering, device in tethering mode, device tethered, button feedback, self-cleaning mode, maintenance required, or other information related to the device. The MCU or peripheral MCU may register, interpret and de-bounce button presses or inputs from other input devices. These presses may be used to enable or adjust: BLE tethering, display battery state of charge, display current sensor readings, sampling/sensing rate or frequency, or any other information or functions relating to the device. In other embodiments the MCU may be used to control and LCD.

The firmware and electronics may be structured such that the device can have its firmware and/or calibration values updated wirelessly. Communication between MCU and a peripheral MCU may use checksums for error correction.

BLE or Other Module

This embodiment of the device uses Bluetooth Low Energy (BLE) for wireless communication with a smart phone or other BLE enabled device. Other embodiments may communicate by cable or other wireless protocol. Other embodiments may not communicate directly but instead transfer data with removable nonvolatile memory (for example a micro SD card). This embodiment may have a low usage mode that sleeps BLE communication on the device between sending sensor data.

BLE communication takes place using a BLE protocol stack, the major components of this stack include, but are not limited to, the following components. On the device side: hardware controller interface, link layer, and physical/device layer. On the application/smart phone side: user application, API, profile layers, host layers, hardware controller interface and physical layer.

Application

The device communicates and is controlled by an application that runs on a smart phone or other BLE enable device. In this embodiment data recorded by the device is sent to the application over FILE and is displayed to the user through a digital interface, including a phone and/or web-based application.

One embodiment of the app may display the current environmental conditions; this may include a comparison of current conditions to other regions and/or recommended actions based on current environment. Another embodiment of the app may display a history of previous environmental conditions, allowing the user to view a log of their historical trends. A further embodiment of the app may display regional maps displaying location-based environmental conditions.

The application may issue various alerts or updates to the user. The application may alert the user when the device is self-cleaning or when user action is required to clean the device. The application may alert the user of hazardous environmental conditions detected by any of the sensors on the device. The application may update itself automatically or prompt the user to update it. The application may update the calibration values of the device depending on historical, geographical, statistical or other types of data. The application may have an API for integration with other applications or devices.

The application may communicate with the device directly over a cable. The communication cable may plug into the existing connector jack on the device. The communication cable may also be used to allow the application to update firmware or calibration values on the device. The communication cable may power the device. The communication cable may communicate or relay all information related to the device.

It should be understood that the foregoing relates to various embodiments of the invention and that modifications may be made without departing from the spirit and scope of the invention. It should also be understood that the present invention is not limited to the designs mentioned in this application and the equivalent designs in this description, but it is also intended to cover other equivalents now known to those skilled in the art, or those equivalents which may become known to those skilled in the art in the future.

INDUSTRIAL APPLICABILITY

The invention pertains to a portable device for detecting and measuring particles entrained in ambient air, which may be of value or importance to various industries such as emissions controls and/or air quality control for research and/or personal health.

What is claimed is:

1. A portable ambient air quality monitor comprising:
A portable environment monitor and tracking system substantially in the vicinity of a user comprising:
an enclosure to enclose and protect the monitor from an environment, the enclosure having a top, a side and a bottom and configured to define an airflow sampling path, an optical path and a sensing region,
the airflow sampling path having an airflow intake and an air channel connected to the airflow intake and an airflow outlet connected to the air channel, the airflow sampling path configured to allow a sampling airflow to enter the monitor through the airflow intake, pass through the air channel and exit the monitor through the airflow outlet, the air channel having
a curved configuration to prevent light entering the airflow sampling path through the airflow intake from passing therethrough and
having at least one baffle within the airflow sampling path proximate the airflow intake to prevent light entering the airflow sampling path through the airflow intake from passing therethrough and for laminarizing the sampling airflow in the air sampling path,
the airflow intake being configured to be perpendicular to the airflow outlet;
the optical path being defined by a photodiode illuminated by a laser beam;
the sensing region being defined by the intersection of the airflow sampling path and the optical path; and;
a sensor within the sensing region to detect and measure particles entrained in the sample airflow, the sensing region comprising a Light Scattering Aerosol Spectrometer (LSAS);
a processor coupled to the sensing region, configured to receive, process and translate data received from the LSAS into particle counts and sizes detected in the ambient air; and
a memory, coupled to the processor, for storing data corresponding to the particle counts and sizes detected in the environment.

2. The portable environment monitor and tracking system according to claim 1 further including a host; and wherein the processor includes an interface to communicate with the host for transmitting the data to the host to allow the user to monitor and track the environment.

3. The portable environment monitor and tracking system according to claim 2, wherein the data is stored on a network.

4. The portable environment monitor and tracking system according to claim 2 wherein the host is a smart phone, personal computer (PC) or a first Bluetooth Low Energy (BLE) device.

5. The portable environment monitor and tracking system according to claim 2, wherein the data is transmitted from the processor to the host or to the network by a wireless communication device or by a communication cable, or to a removable nonvolatile memory device.

6. The portable environment monitor and tracking system according to claim 1 wherein the enclosure further includes a fastener, integrated magnetic fastener, or a clip for affixing the enclosure to the user's clothing, purse, wallet, backpack, jewelry, wristband, flexible band, or bracelet or for affixing the enclosure to the user's body.

7. The portable environment monitor and tracking system according to claim 1 wherein the processor is a microcontroller unit (MCU) or a digital signal processor (DSP).

8. The portable environment monitor and tracking system according to claim 1 wherein the sensor further monitors air quality, temperature, humidity, pressure, visible light, UV radiation, carbon dioxide, carbon monoxide, sound, nitrogen dioxide, magnetic fields, linear accelerations, angular accelerations, ozone and/or gamma, beta, an/or alpha radiation.

9. The portable environment monitor and tracking system according to claim 1 wherein the memory is a removable nonvolatile memory device.

10. The portable environment monitor and tracking system according to claim 1 wherein the system alerts the user of hazardous environmental conditions detected by the sensor.

11. The portable environment monitor and tracking system according to claim 1 wherein the LSAS is configured to count and size particles in the range from 0.5 micrometers to 20 micrometers.

12. The portable environment monitor and tracking system according to claim 1 wherein the system is configured for mesh networking capability to enable data aggregation and pipelining between geospatially networked units and for allowing automatic continuous automatic data homogenization, error compensation, drift compensation and host sharing.

13. A method for monitoring and tracking environment conditions substantially in the vicinity of a user, the method comprising the steps of:
    enclosing and protecting a portable air quality monitor from an environment;
    configuring the monitor to have an airflow sampling path and an optical path,
        the airflow sampling path having an airflow intake and an air channel connected to the airflow intake and an airflow outlet connected to the air channel,
        the optical path being defined by a photodiode illuminated by a laser beam;
    configuring the airflow sampling path and an optical path to intersect to define a sensing region;
    configuring the airflow sampling path to allow a sampling airflow to enter the monitor through the airflow intake, pass through the air channel and exit the monitor through the airflow outlet;
    configuring the air channel to have a curved configuration and to have at least one baffle within the airflow sampling path proximate the airflow intake to prevent light entering the airflow sampling path through the airflow intake from passing therethrough;
    configuring the at least one baffle to laminarize the sampling airflow in the air sampling path to allow a thin stream of the laminarized air to flow into the sensing region;
    directing the laminar airflow into the sensing region;
    sensing the laminar airflow in a sensing region; and
    receiving, processing and translating data received from the sensing region into particle counts and sizes detected in the air; and
    storing the data in a non-transitory computer readable medium corresponding to the particle counts and sizes detected in the environment.

14. The method according to claim 13 further comprising the step of: monitoring air quality, temperature, humidity, pressure, visible light, UV radiation, carbon dioxide, carbon monoxide, sound, nitrogen dioxide, magnetic fields, linear accelerations, angular accelerations, ozone and/or gamma, beta, and/or alpha radiation.

* * * * *